(12) United States Patent
Berelsman et al.

(10) Patent No.: US 7,753,959 B2
(45) Date of Patent: Jul. 13, 2010

(54) MODULAR CENTER PEGGED GLENOID

(75) Inventors: Brian K. Berelsman, Warsaw, IN (US); Russell M. Parrott, Winona Lake, IN (US); Bryce A. Isch, Bluffton, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 76 days.

(21) Appl. No.: 11/385,035

(22) Filed: Mar. 20, 2006

(65) Prior Publication Data

US 2007/0219637 A1    Sep. 20, 2007

(51) Int. Cl.
*A61F 2/40* (2006.01)
(52) U.S. Cl. .................. 623/19.11; 623/19.13
(58) Field of Classification Search ... 623/19.11–19.14, 623/22.21, 22.32, 22.33–22.38, 20.34
See application file for complete search history.

(56) References Cited

U.S. PATENT DOCUMENTS

| | | | |
|---|---|---|---|
| 3,803,641 A | 4/1974 | Golyakhovsky |
| 3,916,451 A | 11/1975 | Buechel et al. |
| 3,979,778 A | 9/1976 | Stroot |
| 4,042,980 A | 8/1977 | Swanson et al. |
| 4,045,825 A | 9/1977 | Stroot |
| 4,045,826 A | 9/1977 | Stroot |
| 4,206,517 A | 6/1980 | Pappas et al. |
| 4,355,429 A | 10/1982 | Mittelmeier et al. |
| 4,550,450 A | 11/1985 | Kinnett |
| D285,968 S | 9/1986 | Kinnett |
| 4,725,280 A | 2/1988 | Laure |
| D295,076 S | 4/1988 | Homsy et al. |
| 4,865,605 A | 9/1989 | Dines et al. |
| 4,919,669 A | 4/1990 | Lannelongue |
| 4,964,865 A | 10/1990 | Burkhead et al. |
| 4,964,867 A | 10/1990 | Boger |
| 4,986,833 A | 1/1991 | Worland |
| 5,030,219 A | 7/1991 | Matsen, III et al. |
| 5,032,132 A | 7/1991 | Matsen, III et al. |

(Continued)

FOREIGN PATENT DOCUMENTS

DE    2041 929    10/1980

(Continued)

OTHER PUBLICATIONS

"Anchor Peg Glenoid, Design Rationale & Surgical Technique," copyright 2002, DePuy Orthopaedics Inc. (10 pgs).

(Continued)

*Primary Examiner*—David H Willse
*Assistant Examiner*—Megan Wolf
(74) *Attorney, Agent, or Firm*—Harness, Dickey

(57) ABSTRACT

A glenoid component used for shoulder arthroplasty is adapted to be implanted into a scapula and engaged by a head of a humeral component. The glenoid component includes a body having a first articulating surface and a second medial surface opposite to the first articulating surface. The first articulating surface is adapted to engage with a humeral head. A plurality of fixed pegs each have a first end adapted to engage a cavity formed in the scapula and a second end extending from the medial surface. A central peg fixation mechanism is provided that is configured to couple an optional central fixation peg to the medial surface.

24 Claims, 8 Drawing Sheets

U.S. PATENT DOCUMENTS

| | | | |
|---|---|---|---|
| 5,080,673 A | 1/1992 | Burkhead et al. | |
| 5,108,446 A | 4/1992 | Wagner et al. | |
| 5,360,452 A * | 11/1994 | Engelhardt et al. | 623/22.37 |
| 5,437,677 A | 8/1995 | Shearer et al. | |
| 5,489,309 A | 2/1996 | Lackey et al. | |
| 5,489,310 A | 2/1996 | Mikhail | |
| 5,549,691 A * | 8/1996 | Harwin | 623/22.37 |
| 5,593,448 A | 1/1997 | Dong | |
| 5,702,447 A | 12/1997 | Walch et al. | |
| 6,102,951 A * | 8/2000 | Sutter et al. | 623/18.11 |
| 6,228,119 B1 | 5/2001 | Ondrla et al. | |
| 6,245,074 B1 | 6/2001 | Allard et al. | |
| 6,364,910 B1 | 4/2002 | Shultz et al. | |
| 6,379,386 B1 | 4/2002 | Resch et al. | |
| 6,406,495 B1 * | 6/2002 | Schoch | 623/19.13 |
| 6,506,214 B1 | 1/2003 | Gross | |
| 6,506,216 B1 * | 1/2003 | McCue et al. | 623/20.34 |
| 6,514,287 B2 | 2/2003 | Ondrla et al. | |
| 6,673,115 B2 | 1/2004 | Resch et al. | |
| 6,699,289 B2 | 3/2004 | Iannotti et al. | |
| 6,761,740 B2 | 7/2004 | Tornier | |
| 6,875,234 B2 | 4/2005 | Lipman et al. | |
| 6,911,047 B2 | 6/2005 | Rockwood, Jr. et al. | |
| 2001/0011192 A1 | 8/2001 | Ondrla et al. | |
| 2001/0037153 A1 | 11/2001 | Rockwood, Jr. et al. | |
| 2002/0082702 A1 | 6/2002 | Resch et al. | |
| 2003/0055507 A1 | 3/2003 | McDevitt et al. | |
| 2003/0125809 A1 | 7/2003 | Iannotti et al. | |
| 2003/0158605 A1 | 8/2003 | Tornier | |
| 2003/0216813 A1 * | 11/2003 | Ball et al. | 623/21.12 |
| 2004/0059424 A1 | 3/2004 | Guederian et al. | |
| 2004/0122519 A1 | 6/2004 | Wiley et al. | |
| 2004/0122520 A1 | 6/2004 | Lipman et al. | |
| 2004/0193276 A1 * | 9/2004 | Maroney et al. | 623/19.14 |
| 2004/0230197 A1 | 11/2004 | Tornier et al. | |
| 2005/0049709 A1 | 3/2005 | Tornier | |
| 2005/0060039 A1 | 3/2005 | Cyprien | |
| 2005/0209700 A1 | 9/2005 | Rockwood, Jr. et al. | |
| 2005/0246028 A1 * | 11/2005 | Pappas et al. | 623/20.25 |
| 2005/0261775 A1 | 11/2005 | Baum et al. | |
| 2007/0162147 A1 * | 7/2007 | Lewis et al. | 623/22.21 |

FOREIGN PATENT DOCUMENTS

| | | |
|---|---|---|
| FR | 2377 798 | 7/1970 |
| FR | 2418 644 | 11/1979 |

OTHER PUBLICATIONS

"The Cofield Total Shoulder System," 1989, by Richards Medical Co., (5 pgs).

"Cementless Total Shoulder Replacement," S. Copeland, pp. 289-293, Surgery of the Shoulder, Edited by M. Post, B.F. Morrey, and R.J. Hawkins. St. Louis, Mosby-Year Book, 1990.

"Cementless Surface Replacement Arthroplasty of the Shoulder 5- to 10- year Results with the Copeland Mark-2 Prosthesis"; Levy, O & S.A. Copeland, J. Bone Joint Surg Brochure p. 213-21, vol. 83B, No. 2, Mar. 2001.

"Resurfacing Arthroplasty of the Shoulder" Copeland, et al., Techniques in Shoulder and Elbow Surgery, pp. 199-210, vol. 4, Issue 4, copyright 2003 Lippincott, Williams & Wilkins Inc.

"Surface Replacement Arthroplasty of the Shoulder," by S. Copeland, et al., article, pp. 1-19, www.readingshoulderunit.com—Journal of Current Orthopaedics 2002, vol. 16, part 1.

* cited by examiner

MODULAR CENTER PEGGED GLENOID

FIELD

The present disclosure relates to a prosthetic device and, more particularly, to a modular glenoid prosthetic.

BACKGROUND

The statements in this section merely provide background information related to the present disclosure and may not constitute prior art. A natural shoulder joint may undergo degenerative changes due to a variety of etiologies. When these degenerative changes become so far advanced and irreversible, it may ultimately become necessary to replace a natural shoulder joint with a prosthetic shoulder joint. When implantation of such a shoulder joint prosthesis becomes necessary, the natural head portion of the humerus can be resected and a cavity is created in the intramedullary canal of the host humerus for accepting a humeral component. The humeral component includes a head portion used to replace the natural head of the humerus. Once the humeral component has been implanted, the glenoid cavity positioned at the lateral edge of the scapula may also be resurfaced and shaped to accept a glenoid component. The glenoid component generally includes an articulating surface which is engaged by the head portion of the humeral component.

It is generally known in the art to provide a shoulder joint prosthesis having a glenoid component, as discussed above. However, the current prior art glenoid components along with the associated surgical components and instruments utilized during shoulder arthroplasty suffer from many disadvantages.

For example, since the glenoid component is subject to various types of loading by the head portion of the humeral component, the glenoid component must offer a stable and secure articulating surface. To achieve this, some glenoid components provide pegs that are inserted and cemented into holes bored into the glenoid cavity. However, such existing pegged glenoid components also exhibit several disadvantages. For example, some of the pegged glenoid components utilize up to five pegs to stabilize and secure the glenoid component to the scapula. Such glenoid components increase the amount of bone tissue removed, while also increasing the labor and complexity of the shoulder arthroplasty. Other pegged glenoid components may offer one or two larger diameter pegs that reduce the complexity of the shoulder arthroplasty. However, the larger diameter pegs also requires excess bone tissue to be removed that may not be practical in some patients. Furthermore, the use of one or two pegs may potentially reduce overall stability of the glenoid component, similar to a keeled glenoid.

Additionally, most prior art glenoid components only rely on the keel or pegs to secure the glenoid component to the scapula, via a cement mantle. These systems are typically rigid in fixation methods. In this regard, the prior art systems fail to provide a selection of coupling mechanisms which may best be used to address varying degenerative changes or specific muscular needs of a patient.

What is needed then is a glenoid component and associated surgical components for use in shoulder arthroplasty that does not suffer from the above-mentioned disadvantages. This in turn, will provide a glenoid component which is stable and secure, reduces the overall amount of bone tissue required to be removed, reduces inventory, reduces the overall surgical time and complexity, increases overall medial surface area, enhances and increases attachment strength and adaptivity without increasing overall peg diameter, provides a fully enhanced coupling mechanism and increased overall stability, and provides increased tensile and shear strength. It is, therefore, an object of the present invention to provide such a glenoid component and associated surgical components for use in shoulder arthroplasty.

SUMMARY OF THE INVENTION

In accordance with the teachings of the present invention, an apparatus and method for shoulder arthroplasty is disclosed. The apparatus and method employs a glenoid component and other associated surgical components for use in the shoulder arthroplasty. In this regard, the glenoid component is adapted to be implanted into a scapula at the glenoid fossa or cavity and engaged by a head portion of a humeral component.

In one embodiment, a glenoid component is used for shoulder arthroplasty such that the glenoid component is adapted to be implanted into a scapula and engaged by a head of a humeral component. The glenoid component includes a body having a first articulating surface and a second medial surface opposite to the first articulating surface. The first articulating surface is adapted to be engaged by the head of the humeral component and the second medial surface is adapted to be secured to the scapula. A plurality of fixed pegs are provided, each having a first end adapted to engage a cavity formed in the scapula and a second end extending from the medial surface. A central peg fixation mechanism is provided that is configured to couple a central fixation peg to the medial surface.

In another embodiment, a system for use during shoulder arthroplasty is provided. The system has a glenoid component adapted to be implanted into a scapula and engaged by a head of a humeral component. The glenoid component includes, a body having a first spherical articulating surface and a second medial surface. The first spherical articulating surface is adapted to permit rotational movement of the head of the humeral component. A plurality of fixed coupling pegs are provided having a first end adapted to engage a cavity formed in the scapula. The medial portion has a central stem fixation mechanism, and a depending central stem.

In another embodiment, a method for implanting a medical device is disclosed. A glenoid prosthetic having a plurality of fixed pegs and a center fixation peg coupling mechanism is provided. The method includes machining a scapula to form a resected glenoid. A plurality of fixed peg accepting holes are machined in the resected glenoid. Further, the scapula is machined to form a center fixation peg coupling member accepting aperture. The physician will then determine if a center fixation peg is needed. If a center peg is required, a center peg is coupled to a glenoid prosthetic. A central peg accepting aperture is optionally machined into the resected glenoid. The prosthetic is then coupled to the resected glenoid either with or without the attached central stem.

Use of the present invention provides an apparatus and method for shoulder arthroplasty, and specifically, a glenoid component and associated surgical components for use in shoulder arthroplasty. As a result, the aforementioned disadvantages associated with the currently available glenoid components and associated surgical components for shoulder arthroplasty have been substantially reduced or eliminated. It should be understood that the detailed description and specific examples, while indicating the preferred embodiment of the invention, are intended for purposes of illustration only and are not intended to limit the scope of the invention.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
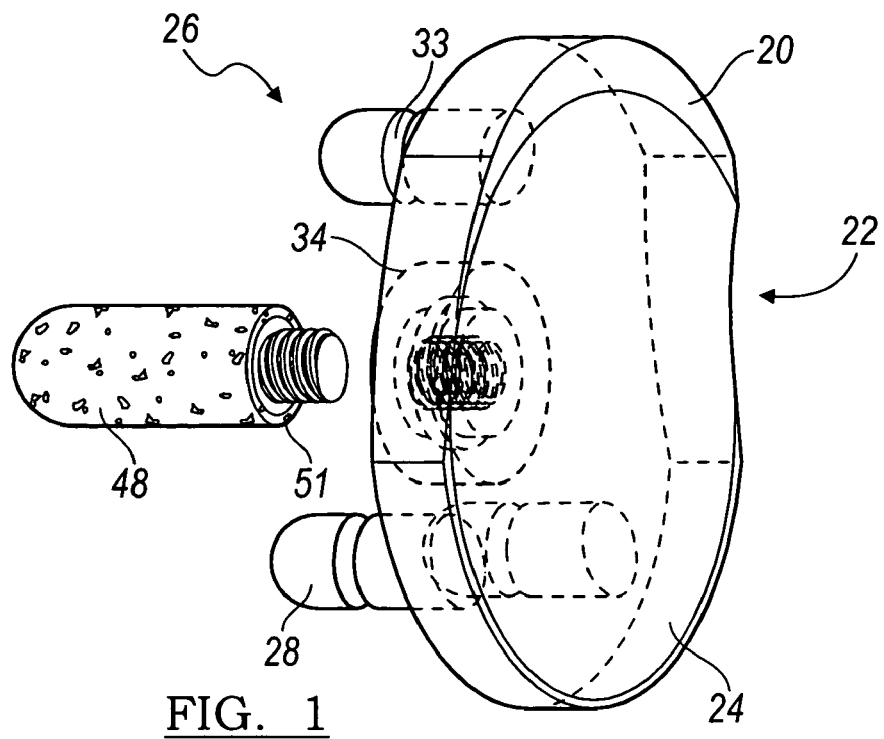
FIG. 1 represents an exploded view of a modular glenoid according to the present teachings of the present disclosure.
Figure 2:
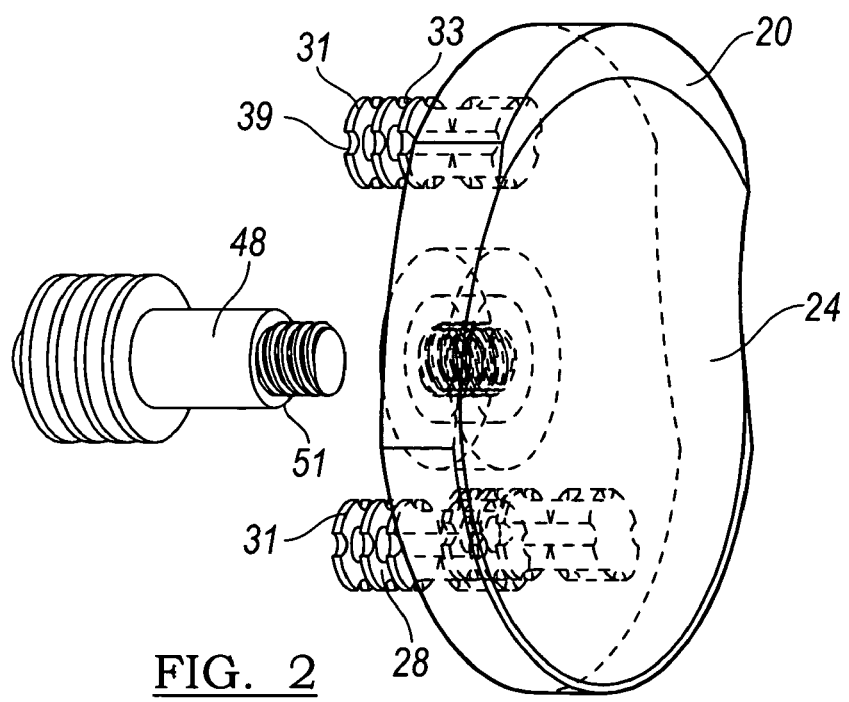
FIG. 2 represents a second glenoid according to the present teachings.

Referring generally to FIGS. 1 and 2 which represent perspective views of the modular glenoid component according to the teachings of the present application. Shown is a glenoid prosthetic 20. The glenoid prosthetic 20 has a first side 22 having a generally spherical articulating surface 24 and a second coupling side 26. The spherical articulating surface 24 is adapted to permit rotational and translational movement of the head of the humeral component (not shown) or natural humerus. The coupling side 26 can include one or more fixed coupling stems 28 that are configured to couple the glenoid to a plurality of apertures defined within a resected glenoid.

The coupling stems 28 can be configured to include a first superior fixed peg 28 and a pair of second inferior fixed pegs 28, each fixed peg 28 positioned on the coupling side 26 to form the corners of a triangle and, preferably, an isosceles triangle. The coupling stems 28 can take on various forms. In this regard, the fixed stems 28 can have a relatively smooth profile which define annular and/or longitudinal grooves 33. As described below, the grooves 33 can be configured to accept bone cement to fixably couple the peg to apertures 35 defined within a resected glenoid 37. As shown in FIG. 2, the fixed glenoid stems 28 can have a plurality of aperture engaging flanges 31. Defined on the flanges 31 can be a plurality of grooves 39. These grooves 39 can be co-axial with grooves 33 defined by the stem 28.

Figure 3A:
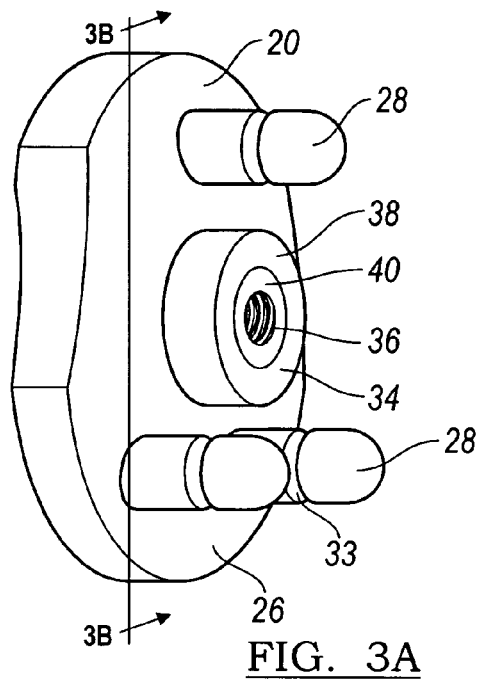
FIGS. 3A and 3B represent perspective and side views of the glenoid according to FIG. 1.
Figure 4A:
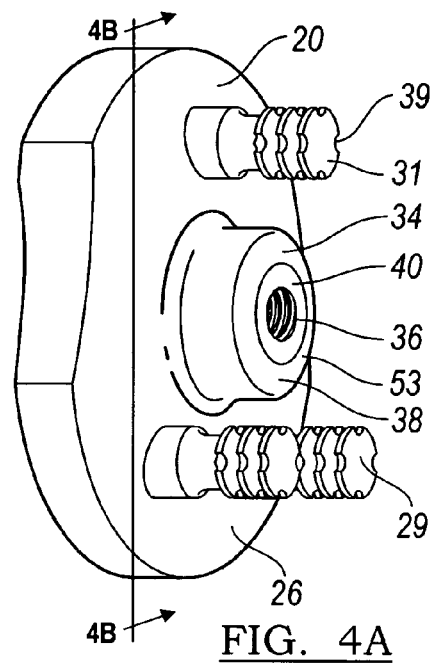
FIGS. 4A and 4B represent perspective and side views of the glenoid according to FIG. 2.
Figure 3B:
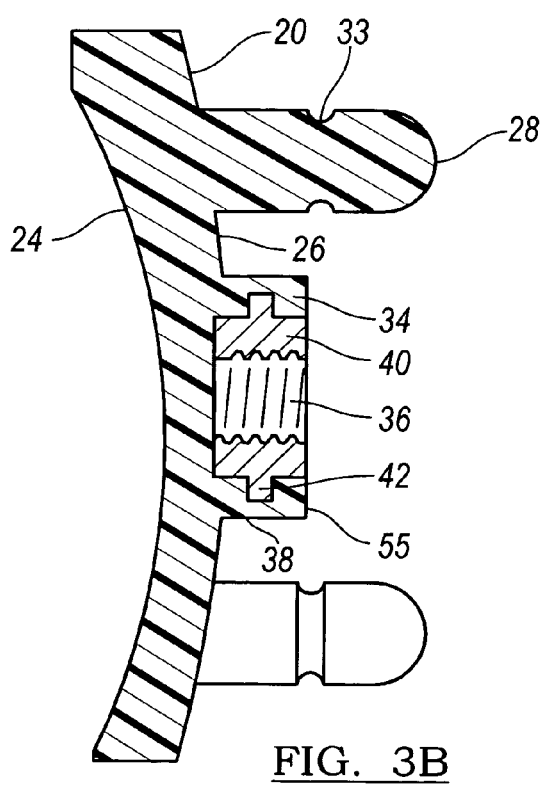
Figure 4B:
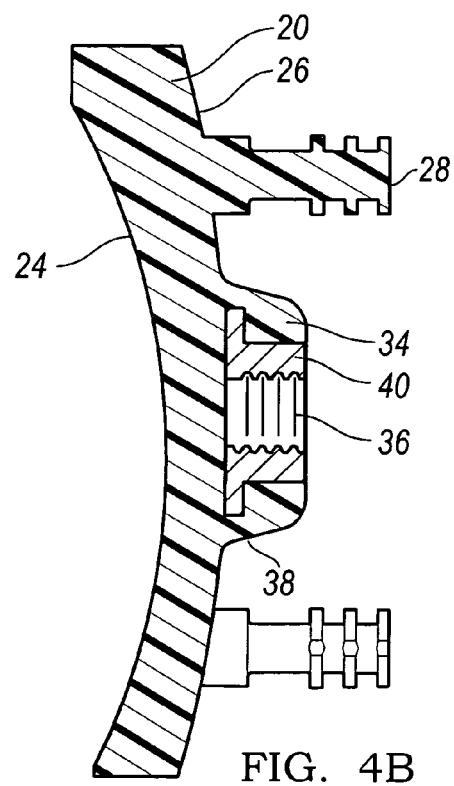
Figure 5A:
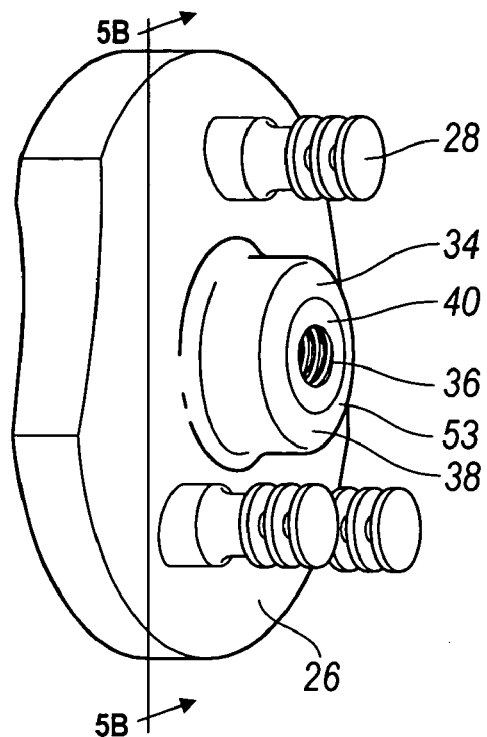
FIGS. 5A and 5B represent alternate perspective and cross-sectional views according to the present teachings.
Figure 5B:
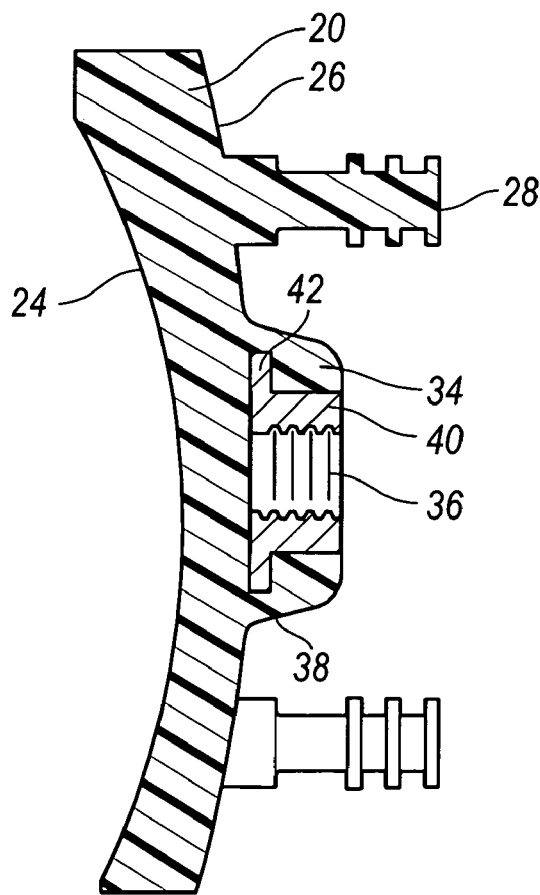

As best seen in FIGS. 3A-3B, the coupling side 26 of the glenoid 20 also defines a central stem coupling mechanism 34. The coupling mechanism 34 is configured to removably and selectively couple a central fixation peg 48 to the coupling side 26. This mechanism can define male or female threaded portions which interface with the central stem 48. As shown, the coupling mechanism 34 can define a threaded coupling aperture 36 within a generally cylindrical body 38. As shown in FIGS. 4A-5B, this cylinder can have a flat or curved exterior surface. In this regard, it is envisioned the exterior surface can be tapered to transition into the coupling side 26. Disposed within the body 38 can be an internally threaded bushing 40. Defined on an exterior surface of the bushing 40 are optional coupling flanges 42 that are configured to couple the bushing 40 to the cylindrical body 38. This bushing can be coupled to the glenoid during a molding process, or the bushing can be press-fit into the coupling side 26.

FIGS. 6A-6E represent perspective and side views of the optional central coupling stems 48. Each of the central coupling stems 48 can have a threaded coupling member 50 which is configured to fixably interface the stem 48 with the threaded aperture 36 of the central coupling mechanism 34. The stems 48 further have a bearing surface or shoulder 51 configured to interface with a bearing surface or base 53 on the central coupling mechanism 34. Optionally, the stems 48 can have a textured coupling surface.

Figure 6A:
FIGS. 6A-6E represent perspective views of various stems usable in the glenoids shown in FIGS. 1-4B.
Figure 6B:
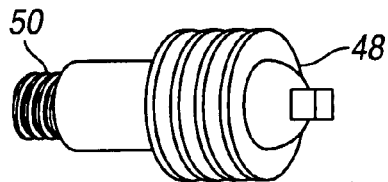
Figure 6C:
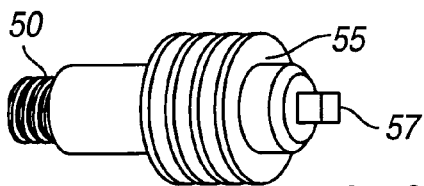
Figure 6D:
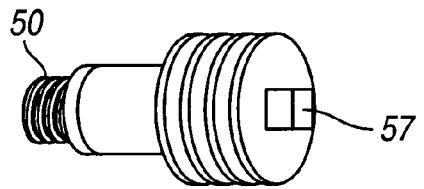
Figure 6E:
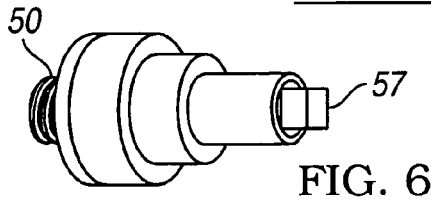

FIG. 6A represents a center peg 48 having a generally cylindrical fixation peg with an exterior powder metal coating. FIGS. 6B-6D represent central pegs having at least one aperture engaging flange. These flanges can either be used to interface with the interior of an aperture formed in the scapula or can be used to retain bone cement in the aperture. FIG. 6E represents a porous central peg having a stepped exterior surface. The stepped exterior surface has varying diameter portions.

Figures 7A, 7B:
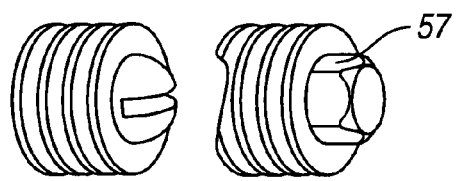
FIGS. 7A-7C represent various drive mechanisms.
Figure 7C:
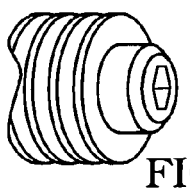
Figure 8A:
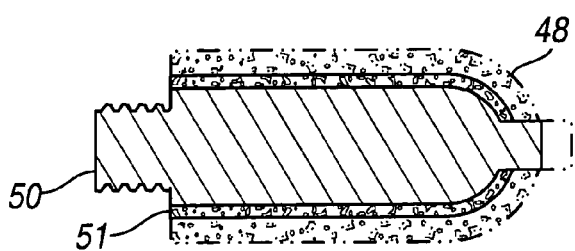
FIGS. 8A-8E represent cross-sectional views of the stems shown in FIGS. 6A-6E.
Figure 8B:
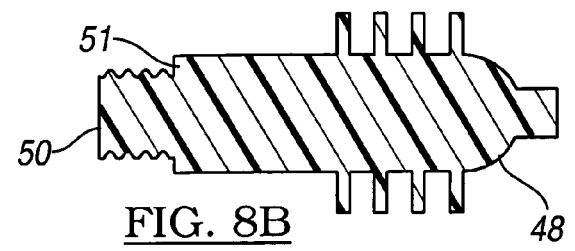
Figure 8C:
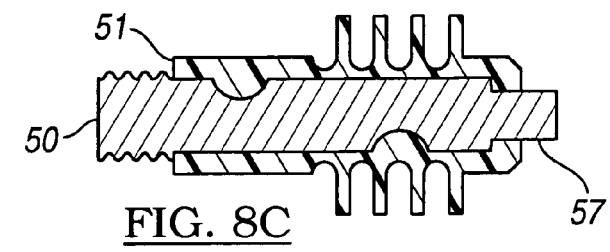
Figure 8D:
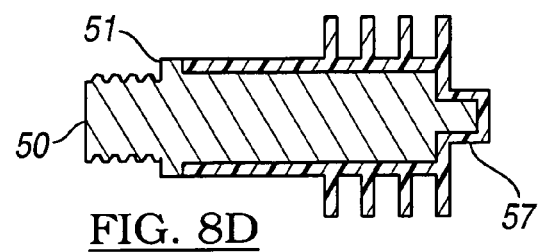
Figure 8E:
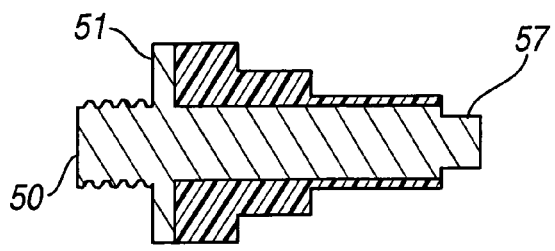

As shown, the central stem 48 can have various surface treatments. It is envisioned the stem can be formed of a biocompatible polymer, metallic or ceramic. Additionally, the central pegs can have surface treatment such as powder metal spray coating or other porous structures to facilitate the ingrowth of bone. As shown in FIGS. 7A-7C, optionally, the stems 48 can have drive surfaces 57 defined on a surface of the stem 48. These drive surfaces 57 can be a multi-faceted extension or a multi-faceted surface defined within a bore in the stem 48.

Shown in FIGS. 8A-8E, the stem can have various cross-sections. In this regard, the diameters of the stems can vary along the length of the stems 48. As shown in FIGS. 6B-6D, the stems 48 can have various coupling flanges 55 incorporated thereon. These coupling flanges 55 can be configured to have an exterior diameter which is less than, equal to, or greater than the corresponding diameter of a portion of an aperture disposed in the resected glenoid 37. Each of the stems 48 is configured to interface with a bearing surface on the central coupling mechanism 34.

Figure 9:
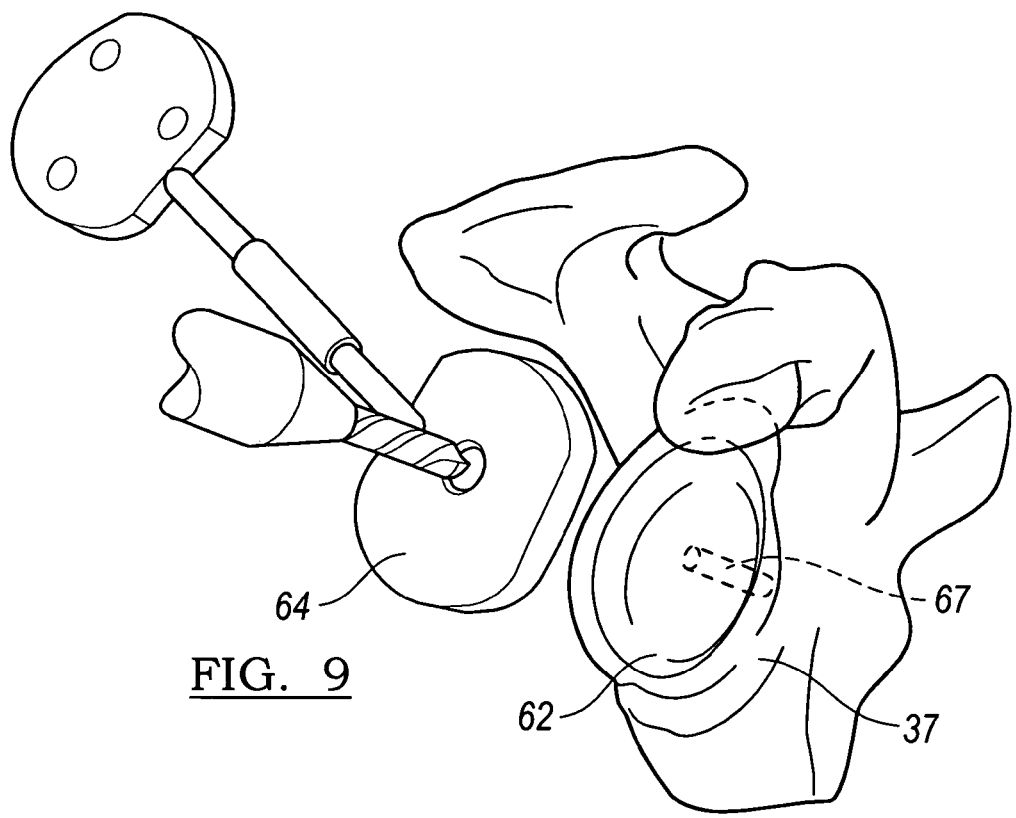
FIGS. 9-12 represent perspective views of the preparation of the glenoid to accept the prosthetic shown in FIGS. 1-8E.
Figure 10:
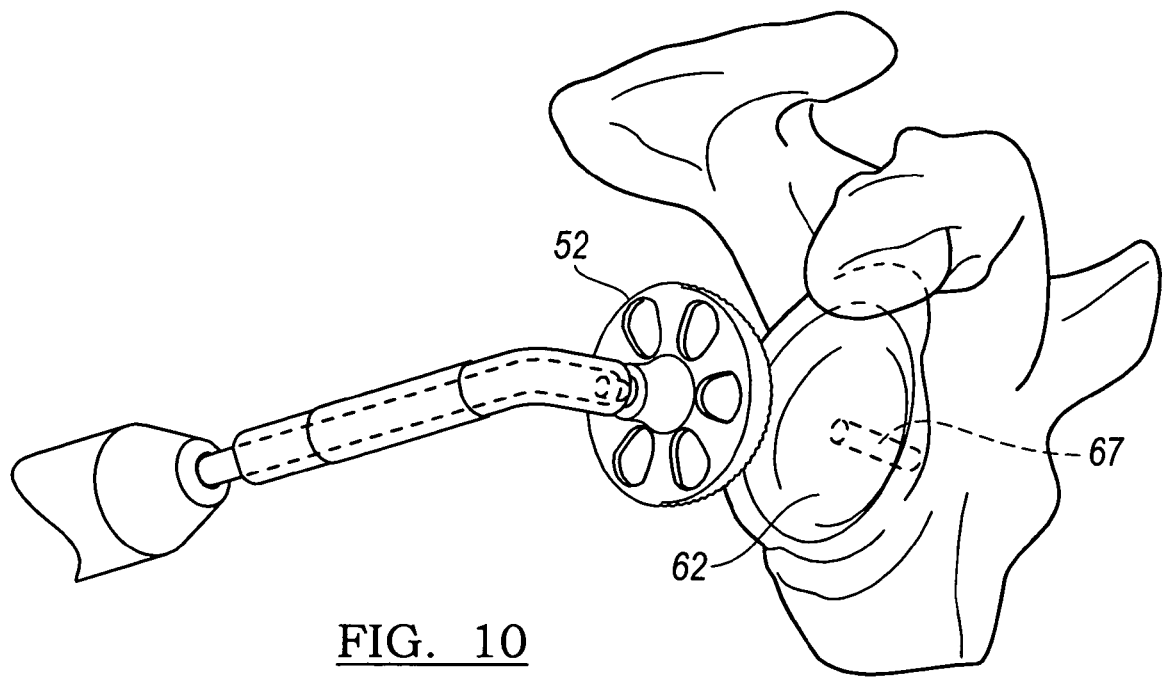

FIGS. 9-13 represent the preparation and insertion of the glenoid 20 according to the teachings herein. As shown in FIG. 9, a second drilling guide 64 can be used to position a central pilot hole 67 into the surface 62. After the preparation of a central guide hole 67, as shown in FIG. 10, the surface of the glenoid 62 is prepared using a rotating rasp or file 52. The scapula is then machined to form the resected glenoid 37. Shown is a rotating rasp 52 used to prepare a planar or curved glenoid surface to mate with the coupling side of the prosthetic 20.

Figure 11:
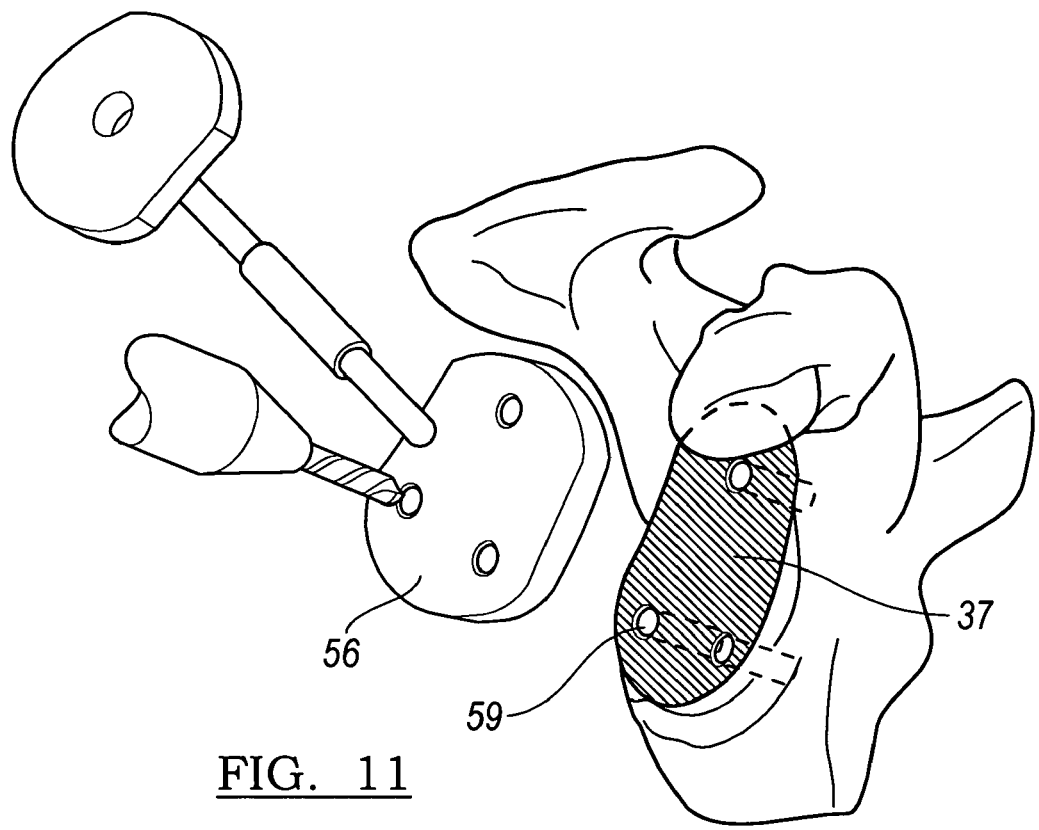
Figure 12:
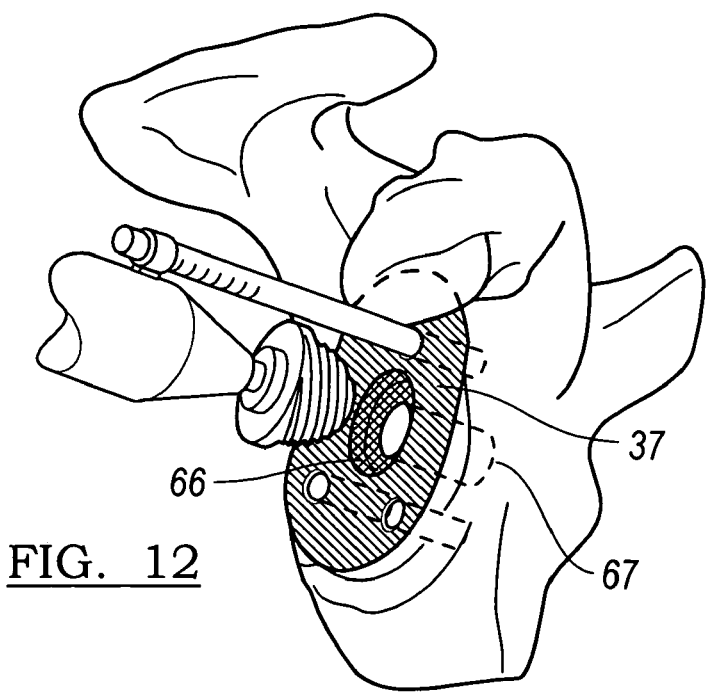

After the resection, a plurality of fixed peg accepting holes 59 are machined into the resected glenoid 37. FIG. 11 represents the use of a drilling guide 56 for the placement of holes within the resected glenoid 37. In this regard, it is envisioned that the drilling guide 56 be used to position the apertures for the acceptance of the fixed stems 28. As shown in FIG. 12, immediately about a central pilot hole, a surface 66 is prepared which is configured to accept the stem coupling mechanism 34. The center stem accepting aperture can be formed either prior to or after the preparation of the surface 66 to accept the stem coupling mechanism 34. At this point, the physician can determine if a central fixation peg 48 is needed. If the central peg 48 is needed, the physician will further determine a preferred central peg fixation surface and a preferred central peg fixation size. The appropriate peg 48 is then chosen and theadably coupled to the glenoid 20 so as to cause engagement of the stem bearing surface 51 with the bearing surface 53 on the central coupling mechanism 34.

Figure 13:
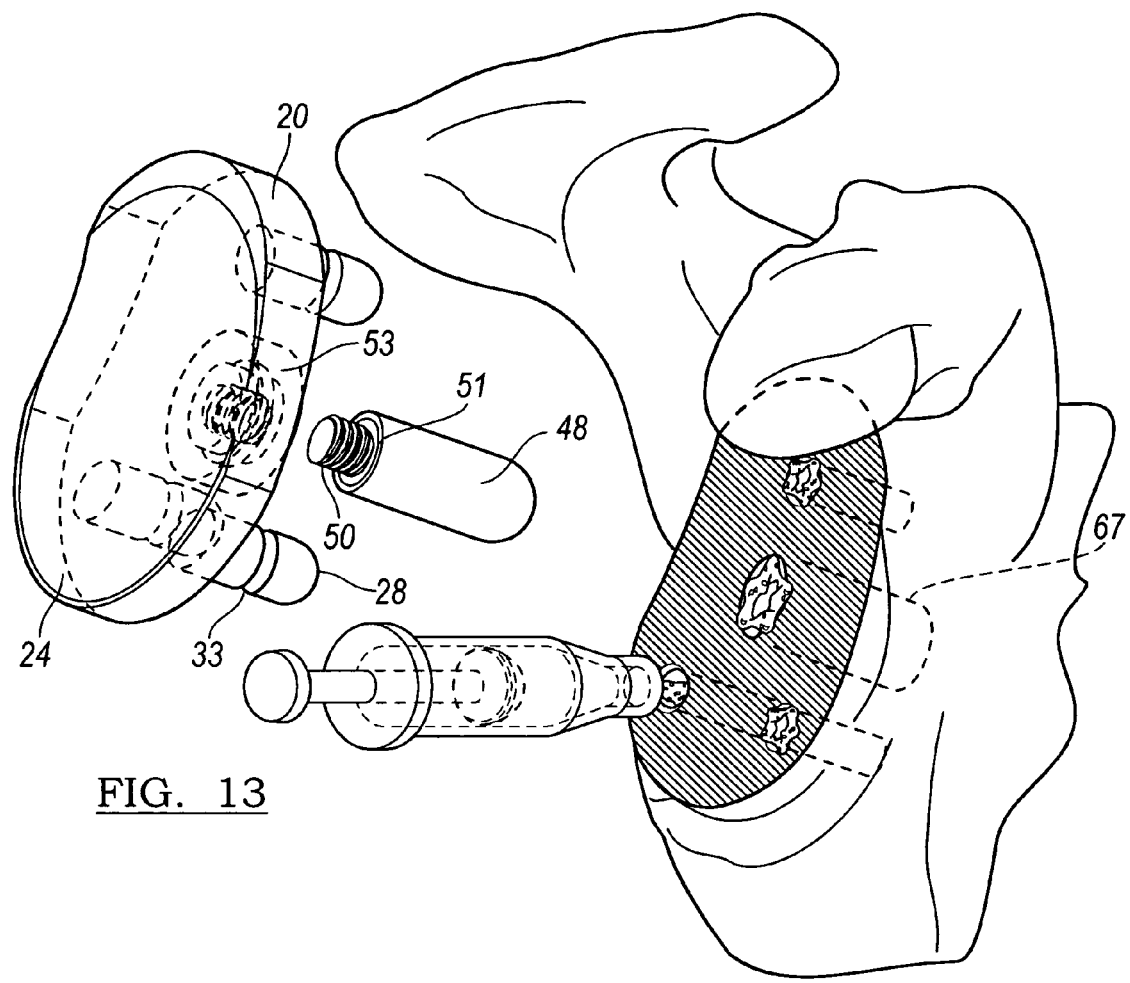
FIG. 13 represents the implantation of the glenoid shown in FIG. 1.

As shown in FIG. 13, it is envisioned that bone cement or biological materials can be injected into the apertures defined within the resected glenoid 37. These materials can be inserted into the holes configured to accept the fixed pegs or the central stem 48. It is equally envisioned that the central stem 48 can be inserted into the aperture so as to form an interference fit between the central stem 48 and the aperture. With the appropriate coupling stem 48 fixed to the bushing within the coupling mechanism 34, proper coupling of the glenoid 20 can occur. In this regard, the central stem 48 is threadably coupled to an aperture within the central stem coupling mechanism 34. The fixed and central stems are positioned within the apertures to couple the glenoid member 20 to the resected glenoid 37.

Figure 14:
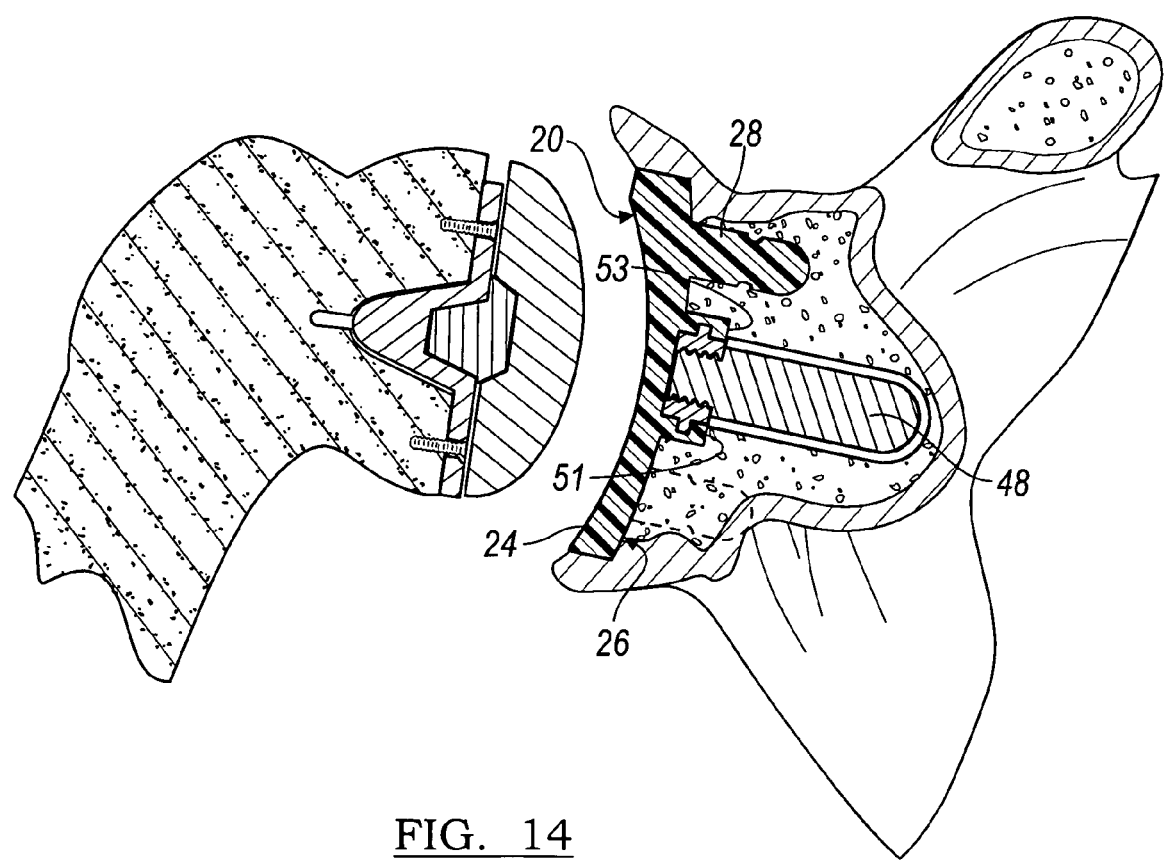
FIG. 14 represents a side cross-sectional view of a glenoid according to the present teachings implanted into a resected glenoid.

FIG. 14 represents a cross-sectional view of an implanted glenoid 20. Shown is the relationship between the articulating surface 24, fixed stems 28, and the central stem 48. Optionally, the coupling side 26 can be bonded to the resected glenoid using bone cement and further can have surface treatments to facilitate bonding. Further shown is the central stem 48 in relation to the threaded aperture 36 of the central stem coupling mechanism 34.

Figure 15:
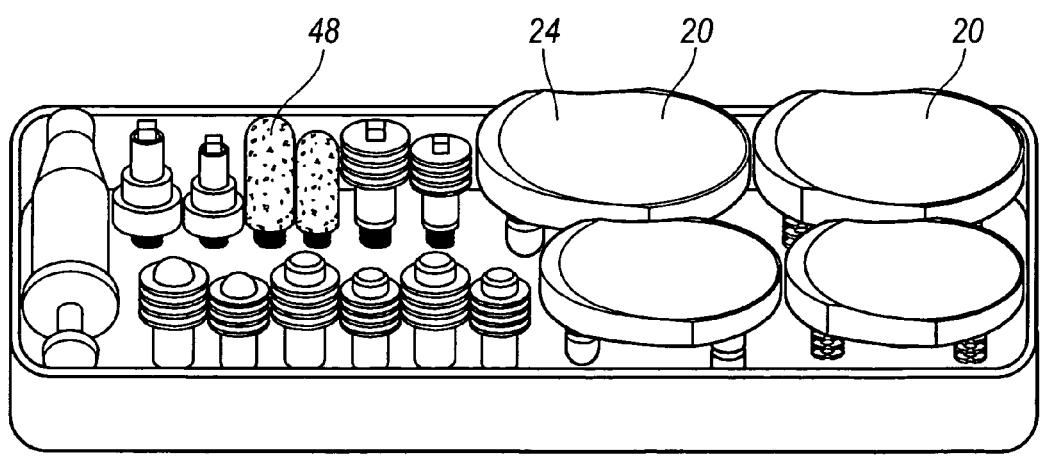
FIG. 15 represents a system of modular glenoid components according to the present teachings.

FIG. 15 represents a system of prosthetic components as described above. Shown are various glenoid prosthetics 20 as well as various size and shaped central stem portions 48. These stems 48 have various exterior surface treatments and configurations as well as varying lengths and diameters. It is envisioned that the system also includes the appropriate types of bone fixation cement, cutting members, cutting pattern guides, as well as humeral head and fixation stem prosthetics.

What is claimed is:

1. A system for use during shoulder arthroplasty, said system having a glenoid component adapted to be implanted into a scapula and engaged by a head of a humeral component, said glenoid component comprising:
    a body having a first articulating surface and a second medial surface opposite said first articulating surface, said first articulating surface adapted to be engaged by a humeral head and said second medial surface adapted to be secured to the scapula, a generally cylindrical coupling mechanism protruding from said second medial surface, said coupling mechanism having a first flat bearing surface;
    a metal bushing integrally molded within the coupling mechanism, said metal bushing defining a threaded central bore;
    at least one fixed peg, each of said fixed pegs having a first end adapted to engage a cavity formed in the scapula and a second end extending from said medial surface; and
    a removable central stem, said central stem further having a second exterior flat bearing surface, the second exterior flat bearing surface configured to interface with the first flat bearing surface when the removable central stem is engaged with the threaded central bore before the body is engaged with the scapula, said central stem being configured to be non-rotatably engaged with a hole defined in the scapula.

2. The system as defined in claim 1 wherein said first articulating surface has a spherical concave surface adapted to permit rotational and translational movement of the head of the humeral component.

3. The system as defined in claim 1 wherein said central stem includes a textured coupling surface.

4. The system as defined in claim 3 wherein said textured coupling surface includes one of a porous coating or a porous metal.

5. The system as defined in claim 1 wherein the at least one fixed peg defines at least one of a bone cement retaining groove and a plurality of bone cement retaining flanges.

6. The system as defined in claim 1 wherein said at least one fixed peg includes a first superior fixed peg and a pair of second inferior fixed pegs, each fixed peg positioned on said second medial surface to form the corners of an isosceles triangle.

7. The system as defined in claim 1 wherein a central stem is defined by a generally cylindrical outer peripheral surface, said central stem including a fixation thread.

8. The system as defined in claim 1 wherein each of said at least one fixed pegs includes a textured surface.

9. The system as defined in claim 1 comprising a plurality of central fixation pegs.

10. A system for use in shoulder arthroplasty, said system having a glenoid component adapted to be implanted into a scapula, said system comprising:
    a body having a first articulating surface and a second medial surface opposite said first articulating surface, said second medial surface adapted to be secured to the scapula;
    a central cylindrical stem coupling mechanism having a fixed metal bushing integrally molded within the central cylindrical stem coupling mechanism and defining a threaded aperture disposed therein, said central cylindrical stem coupling mechanism protruding from the second medial side; and
    a plurality of central stems removably and selectively couplable to the central cylindrical stem coupling mechanism, wherein the stems vary in size, one of said plurality of stems having a flat exterior bearing surface configured to engage the central cylindrical stem coupling mechanism.

11. The system as defined in claim 10 wherein one of said central stems includes an enhanced textured surface.

12. The system as defined in claim 11 wherein said enhanced textured surface includes a porous coating.

13. The system as defined in claim 10 wherein the second medial surface comprises a plurality of fixed pegs which define a bone cement retaining groove.

14. The system as defined in claim 13 wherein the fixed pegs define a plurality of bone cement retaining flanges.

15. The system as defined in claim 13 wherein said plurality of fixed pegs comprise a first superior fixed peg and a pair of second inferior fixed pegs.

16. The system as defined in claim 10 wherein the central stem coupling mechanism is defined by a generally cylindrical outer peripheral surface.

17. The system as defined in claim 10 wherein the metal bushing has a retaining ring.

18. A method for implanting a medical device, the method comprising:
    shaping a scapula to receive a glenoid prosthetic;
    selecting a center fixation peg from a plurality of pegs;
    coupling the center fixation peg to a bore defined by a fixed metal bushing integrally molded within a generally cylindrical coupling mechanism of a glenoid prosthetic so as to position a coupling mechanism bearing surface on the center fixation peg against a center fixation peg bearing surface on the coupling mechanism, said glenoid prosthetic having a plurality of fixed fixation pegs; and coupling the glenoid prosthetic to the scapula after coupling the center fixation peg to the bore, wherein coupling a center fixation peg to the glenoid prosthetic further includes determining at least one of an appropriate central peg fixation surface and a central peg fixation size.

19. The method according to claim 18 wherein coupling a center fixation peg to a glenoid prosthetic is threadably coupling the center fixation peg to a threaded aperture defined by the metal bushing.

20. The method according to claim 18 further comprising shaping a plurality of fixed peg accepting apertures within the scapula.

21. The method according to claim 20 further comprising placing bone cement within the plurality of fixed peg accepting apertures.

22. The method according to claim 18 further comprising selecting a center fixation peg having an appropriate central peg fixation surface.

23. The method of claim 18 further comprising shaping the scapula to receive the glenoid prosthetic by machining an aperture within the scapula, the aperture having a first diameter for accepting the center fixation peg and a second diameter for accepting the coupling mechanism.

24. The method of claim 23, wherein the second diameter is greater than the first diameter.

* * * * *